United States Patent [19]

Miller, Jr.

[11] Patent Number: 5,492,693
[45] Date of Patent: Feb. 20, 1996

[54] COMPOSITIONS FOR TREATING ANIMALS AND SURFACES INFESTED WITH ECTOPARASITES

[75] Inventor: Gordon G. Miller, Jr., Richmond, Va.

[73] Assignee: Safety Pet Products Inc., Richmond, Va.

[21] Appl. No.: 396,669

[22] Filed: Mar. 1, 1995

Related U.S. Application Data

[63] Continuation-in-part of Ser. No. 286,919, Aug. 8, 1989, Pat. No. 5,456,913, which is a continuation-in-part of Ser. No. 142,799, Oct. 25, 1993, abandoned.

[51] Int. Cl.$^6$ .................. A01N 65/00; A01N 59/10; A01N 59/08
[52] U.S. Cl. .................. 424/195.1; 424/676; 424/680; 514/876; 514/919; 119/158
[58] Field of Search ............... 424/195.1, 676, 424/680; 514/876, 919; 119/158

[56] References Cited

U.S. PATENT DOCUMENTS

| | | | |
|---|---|---|---|
| 4,193,986 | 3/1980 | Cox | 424/411 |
| 4,342,743 | 8/1982 | Panton-Moore | 424/61 |
| 4,374,853 | 2/1983 | Workman | 514/506 |
| 4,379,168 | 4/1983 | Dotolo | 514/763 |
| 4,668,434 | 5/1987 | Bowman | 252/522 |
| 4,808,615 | 2/1989 | Ott et al. | 514/89 |
| 4,874,753 | 10/1989 | Baker | 514/89 |
| 4,935,248 | 6/1990 | Witkin | 424/616 |
| 4,973,589 | 11/1990 | Barnett et al. | 514/245 |
| 5,017,615 | 5/1991 | Workman | 514/560 |
| 5,066,497 | 11/1991 | Witkin | 424/616 |
| 5,084,281 | 6/1992 | Dillon | 424/677 |
| 5,194,264 | 3/1993 | Van Tonder | 424/405 |
| 5,221,535 | 6/1993 | Domb | 424/450 |

*Primary Examiner*—John W. Rollins
*Attorney, Agent, or Firm*—Leydig, Voit & Mayer, Ltd.

[57] ABSTRACT

Compositions for treating animals and surfaces infested with ectoparasites are provided for. The compositions comprise providing a solution consisting essentially of water and sea salt. The solution preferably includes a dissolved skin conditioner, preferably a natural skin conditioner, such as oat grains. The solution is applied to any animal, by dipping, spraying or in an aqueous-based carrier such as a shampoo, in an amount and for a period of time sufficient to deinfest the animal. The composition can be applied in dry form to carpets or lawns where animals lie to prevent infestation or reinfestation of the animal.

15 Claims, No Drawings

COMPOSITIONS FOR TREATING ANIMALS AND SURFACES INFESTED WITH ECTOPARASITES

This application is a continuation in part of U.S. Ser. No. 08/286,919, filed Aug. 8, 1994, now U.S. Pat. No. 5,456,913 which is a continuation in part of U.S. Ser. No. 08/142,799, filed on Oct. 25, 1993, now abandoned.

FIELD OF THE INVENTION

This invention relates to compositions useful for treating animals and surfaces which are infested with fleas, ticks, and other ectoparasites, and in particular, to such compositions which comprise natural, nontoxic ingredients.

BACKGROUND OF THE INVENTION

The problems associated with animals such as pets which are infested with fleas, ticks, and other ectoparasites are well known. There are a wide variety of dips, sprays, powders, shampoos, collars, and the like which are designed to rid animals of such pests. Many are effective. The product in dry form can be sprinkled on carpets or lawns where pets lie. It could be sprayed on lawns in a mixture with water. Further, existing treatments may contain relatively expensive ingredients and may require careful formulation and application to achieve satisfactory results while avoiding potentially harmful effects.

It is an object of the subject invention, therefore, to provide a composition which is effective in treating animals infested with ectoparasites, but which also is composed of natural, nontoxic ingredients which are safe to a pet, a pet owner, and to the environment. Another object of the subject invention is to provide such compositions which incorporate inexpensive ingredients which are easily formulated, packaged, and applied.

Those and other objects and advantages of the present invention will be apparent from the following description.

SUMMARY OF THE INVENTION

The subject invention is based on applicant's observation that a solution of sea salt is effective in ridding animals of fleas and ticks. The solution preferably includes a dissolved skin conditioner, preferably a natural skin conditioner, such as oats. The solution then is applied to the animal, preferably by dipping the animal, in an amount and for a period of time sufficient to deinfest the animal.

It will be appreciated, therefore, that the composition of the subject invention not only is effective in deinfesting an animal, but that the compositions are composed essentially of natural ingredients which are safe to pets and humans and pose little risk to the environment, especially as compared to many synthetic chemical-based treatments. In dry form the composition is in a fine particle state which can be sprinkled on carpets or lawn areas where pets most often lie.

DETAILED DESCRIPTION OF THE INVENTION

The compositions of the subject invention utilize sea salt to deinfest an animal carrying ectoparasites. Sea salt is produced by evaporation or from mining of deposits and is commercially available from many sources, e.g., for use in home aquariums. In general, commercial grade sea salt may be used in the subject invention. Although the reasons for this are not fully understood, however, it has been observed that sea salt obtained from CARGILL Salt Division, P.O. Box 5621, Minneapolis, Minn. 55440 or CARGILL Leslie Salt Co., 7220 Central Avenue, Newark, Calif. 94560-4206, is particularly effective.

The sea salt is dissolved in water for application to an animal. Accordingly, the sea salt is provided in a form which will facilitate its dissolution into water, such as finely divided crystals. Because salt is highly soluble in water, however, the size of the salt crystals is not critical. The water also may be heated slightly to facilitate dissolution, especially if the sea salt is not finely divided. Further, as discussed below, it may be advantageous to pelletize the salt.

The sea salt will be dissolved in water in concentrations sufficient to deinfest an animal. By deinfest, it is meant simply that the ectoparasites are either killed, incapacitated, or otherwise driven off an animal. It is expected that sea salt in a concentration of about 1 cup per from about 10 to about 16 gallons of water will be effective. It will be appreciated, however, that the optimum amount will vary somewhat, for example, depending on the inherent efficacy of a particular grade of sea salt.

Likewise, the animal will be treated for a time sufficient to allow deinfestation of the animal. In general, this will require treatment for about 5 to about 20 minutes. The precise time of treatment, however, may vary somewhat. More concentrated solutions will require shorter treatment times. More heavily infested animals may require longer treatment times.

The sea salt solution may be applied by any suitable method, such as spraying. Because an animal must be exposed to the solution for a significant period of time, during which the animal may be inclined to shake off the solution, however, dipping the animal in a bath of the sea salt solution is preferred. Preferably the temperature of the bath will be comfortable to the animal, but otherwise, the temperature is not believed to be critical.

Preferably, the sea salt solution also includes a conditioner to minimize drying of an animal's skin which otherwise might occur as a consequence of frequent bathing. Preferably, the skin conditioner is a dry, water-soluble natural ingredient, such as oats. Such conditioners preferably are finely ground to facilitate their dissolution in water. Many other water-soluble conditioners are known, however, and in general may be used in the subject invention.

The amount of skin conditioner incorporated in the sea salt solution can vary greatly. Preferably, there is an amount sufficient to compensate for drying of an animal's skin which may be caused by frequent bathing. On the other hand, little benefits will be obtained by using excessively large amount of skin conditioner. For example, when oats and the like are used as a skin conditioner, it is expected that one part conditioner per from about 6 to about 9 parts of sea salt would provide satisfactory results.

The sea salt, along with any desired skin conditioner, preferably is compounded and packaged in a dry state for mixing with water immediately prior to use by a consumer. The sea salt and skin conditioner, however, can be packaged as a liquid concentrate. The sea salt, and any added skin conditioner, also can be pelletized, with binders if necessary, for example, in a pellet of a predetermined quantity sufficient for a single bath.

It will be appreciated, therefore, that the novel solutions may be easily formulated and applied. The ingredients are easily handled and shipped, especially if packaged as a dry concentrate for mixing immediately prior to use. The concentrate can be easily mixed with water by a consumer. The concentrate will be effective in solutions having a relatively wide range of concentrations, giving a consumer a wide margin of error in mixing a bath. Sea salt also is very inexpensive and is nontoxic.

The invention is further described by reference to the following example. It is not intended to limit the scope of the invention; rather, it is presented merely to facilitate the practice of the invention by those of ordinary skill in the art and to further disclose the inventor's best mode of doing so.

EXAMPLE 1

A dry mixture of 95 wt. % sea salt (obtained from Cargill Leslie Salt Co.) and 5 wt. % finely ground oats was compounded together. One-half cup of the dry mixture was dissolved in eight gallons of water to produce a bath.

Flea and tick infested dogs were treated by dipping them in the bath for from about 5 to about 10 minutes. It was observed that within approximately 5–8 minutes that the fleas and ticks began to appear to become bloated and to float to the surface of the bath. The fleas and ticks eventually were killed, some apparently having burst, and sank to the bottom of the bath. After the treatment, the animals were observed to be substantially free from ticks and fleas.

This invention has been disclosed and discussed primarily in terms of specific embodiments thereof, but it is not intended to be limited thereto. Other modifications and embodiments will be apparent to workers in the art.

It has also been found that application of the composition of the present invention to carpets and lawns in areas where the pets will most frequently lie will prevent infestation or reinfestation of the pet by fleas and ticks. Since the composition is initially provided in fine particle form it can be sprinkled in small areas of carpets or lawns. The composition will not harm the carpet or lawns and in the case of carpets it comes out easily during ordinary vacuuming. For applications to larger areas of lawns, the composition can be applied by spraying a solution such as by using a conventional lawn or garden spray device either self contained or attached to a garden hose.

I claim as my invention:

1. A solution for treating animals infested with ectoparasites consisting of water, sea salt in an amount effective to deinfest an animal, and a skin conditioner.

2. The solution of claim 1, wherein the solution consists of about 1 cup per from about 10 to about 16 gallons of water.

3. The solution of claim 2, wherein the skin conditioner is present in an amount equal to weight part per from about 6 to about 9 weight parts sea salt.

4. The solution of claim 1, wherein the skin conditioner is ground oat grains.

5. A solution of claim 1, wherein the solution further consists of an aqueous based shampoo.

6. The solution of claim 1, wherein the skin conditioner is present in an amount equal to weight part per about 19 weight parts sea salt.

7. A mixture for treating animals and surfaces infested with ectoparasites, the mixture consisting of one weight part ground oat grains per from about 6 to about 9 weight parts sea salt.

8. The mixture of claim 7, wherein the mixture further consists of an aqueous based shampoo.

9. A water soluble mixture suitable for formulating an aqueous bath for treating animals infested with ectoparasites, the mixture consisting essentially of sea salt, an aqueous based shampoo and a skin conditioner.

10. The mixture of claim 9, wherein the mixture consists of one weight part skin conditioner per from about 6 to about 9 weight parts sea salt.

11. The mixture of claim 9, wherein the mixture consists essentially of one weight part skin conditioner per about 19 weight parts sea salt.

12. The mixture of claim 11, wherein the skin conditioner is ground oat grains.

13. The mixture of claim 10, wherein the skin conditioner is ground oat grains.

14. A water soluble dry mixture for treating animals or surfaces infested with ectoparasites when the mixture is dissolved in an aqueous solution and applied to an infested animal or surface consisting of 6–9 weight parts of sea salt and 1 weight part of ground oat grains.

15. A mixture for treating animals infested with ectoparasites consisting essentially of oat grains as a skin conditioner and sea salt in an amount effective to deinfest an animal when said mixture is in solution.

* * * * *